United States Patent
Austen, Jr. et al.

(10) Patent No.: US 10,292,381 B2
(45) Date of Patent: May 21, 2019

(54) VESSEL TREATMENT SYSTEMS, METHODS, AND KITS

(71) Applicant: The General Hospital Corporation, Boston, MA (US)

(72) Inventors: William G. Austen, Jr., Weston, MA (US); Michael C. McCormack, Medford, MA (US); Robert C. Redmond, Lancaster, MA (US); Irene E. Kocheavar, Boston, MA (US)

(73) Assignee: The General Hospital Corporation, Boston, MA (US)

( * ) Notice: Subject to any disclaimer, the term of this patent is extended or adjusted under 35 U.S.C. 154(b) by 94 days.

(21) Appl. No.: 14/992,733

(22) Filed: Jan. 11, 2016

(65) Prior Publication Data

US 2016/0120173 A1 May 5, 2016

Related U.S. Application Data

(63) Continuation of application No. PCT/US2014/047146, filed on Jul. 18, 2014.
(Continued)

(51) Int. Cl.
*A01N 1/02* (2006.01)
*A61M 1/36* (2006.01)

(52) U.S. Cl.
CPC ......... *A01N 1/0242* (2013.01); *A61M 1/3655* (2013.01)

(58) Field of Classification Search
CPC ... A01N 1/0242; A61M 1/3655; A61N 5/062; A61N 5/0616; A61N 2005/0645; A61N 2005/0649
See application file for complete search history.

(56) References Cited

U.S. PATENT DOCUMENTS 2,127,903 A 8/1938 Bowen
3,798,688 A * 3/1974 Wasson ............. A61B 17/3213
30/353
(Continued)

FOREIGN PATENT DOCUMENTS

EP 0627911 B1 10/2000
EP 1229937 B1 11/2007
(Continued)

OTHER PUBLICATIONS

Sung, et al., "Crosslinking of biological issues using genipin and/or carbodiimide" (2003).
(Continued)

*Primary Examiner* — Kaylee R Wilson
(74) *Attorney, Agent, or Firm* — Saul Ewing Arnstein & Lehr LLP; Peter C. Lauro; Brian R. Landry

(57) ABSTRACT

One aspect of the invention provides a vessel treatment system including: a housing defining at least one opening adapted and configured to receive an anatomical vessel; and a humidifier in communication with the housing, the humidifier adapted and configured to introduce humidity into the housing to prevent desiccation of the anatomical vessel. Another aspect of the invention provides a kit including: the vessel treatment system as described herein; and a passivation agent. Another aspect of the invention provides a method for preparing a vein graft. The method includes: applying a tissue passivation agent to a resected anatomical vessel; and placing the resected anatomical vessel in a humidified chamber while the tissue passivation agent cures.

3 Claims, 4 Drawing Sheets

Related U.S. Application Data

(60) Provisional application No. 61/847,794, filed on Jul. 18, 2013.

(56) References Cited

U.S. PATENT DOCUMENTS

| | | | |
|---|---|---|---|
| 3,916,874 A | 11/1975 | Perrin | |
| 4,083,066 A | 4/1978 | Schmitz et al. | |
| 4,127,109 A | 11/1978 | Fourney et al. | |
| 4,383,832 A | 5/1983 | Fraefel et al. | |
| 4,612,938 A | 9/1986 | Dietrich | |
| 4,662,884 A | 5/1987 | Stensaas | |
| 4,870,966 A | 10/1989 | Dellon et al. | |
| 4,908,013 A | 3/1990 | Muller et al. | |
| 5,002,583 A | 3/1991 | Pitaru et al. | |
| 5,125,925 A | 6/1992 | Lundahl | |
| 5,147,514 A * | 9/1992 | Mechanic | A61L 27/3683 204/157.68 |
| 5,209,776 A | 5/1993 | Bass et al. | |
| 5,241,781 A * | 9/1993 | Malczyk | A01G 9/00 47/17 |
| 5,292,362 A | 3/1994 | Bass et al. | |
| 5,374,515 A | 12/1994 | Parenteau et al. | |
| 5,376,110 A | 12/1994 | Tu et al. | |
| 5,376,376 A | 12/1994 | Li | |
| 5,431,790 A | 7/1995 | Nesburn et al. | |
| 5,552,452 A | 9/1996 | Khadem et al. | |
| 5,565,551 A | 10/1996 | Lewis et al. | |
| 5,571,216 A | 11/1996 | Anderson | |
| 5,616,562 A | 4/1997 | Murphy et al. | |
| 5,686,303 A | 11/1997 | Korman | |
| 5,709,653 A | 1/1998 | Leone | |
| 5,749,968 A | 5/1998 | Melanson et al. | |
| 5,829,448 A | 11/1998 | Fisher et al. | |
| 5,844,016 A | 12/1998 | Sawhney et al. | |
| 5,917,045 A | 6/1999 | Lewis et al. | |
| 6,017,466 A | 1/2000 | Fujino et al. | |
| 6,030,974 A | 2/2000 | Schwartz et al. | |
| 6,364,874 B1 | 4/2002 | Bays | |
| 6,425,912 B1 * | 7/2002 | Knowlton | A45D 44/22 606/33 |
| 6,468,244 B1 | 10/2002 | Leone | |
| 6,511,494 B1 * | 1/2003 | Knighton | A61B 17/00008 606/190 |
| 6,607,522 B1 | 8/2003 | Hamblin et al. | |
| 6,773,699 B1 | 8/2004 | Soltz et al. | |
| 6,783,539 B1 | 8/2004 | Timberlake et al. | |
| 7,022,524 B1 * | 4/2006 | Phillips | A01N 37/02 435/420 |
| 7,037,490 B2 | 5/2006 | Rowe | |
| 7,073,510 B2 | 7/2006 | Redmond | |
| 7,331,350 B2 | 2/2008 | Kochevar et al. | |
| 7,465,312 B2 | 12/2008 | O'Dowd et al. | |
| 8,092,490 B2 | 1/2012 | Redmond et al. | |
| 8,172,788 B2 | 5/2012 | Konincks et al. | |
| 8,215,314 B2 | 7/2012 | Chan | |
| 8,512,695 B2 | 8/2013 | Austen, Jr. | |
| 2002/0006394 A1 | 1/2002 | Redmond et al. | |
| 2002/0022588 A1 | 2/2002 | Wilkie et al. | |
| 2002/0022606 A1 | 2/2002 | Kochevar et al. | |
| 2002/0077697 A1 | 6/2002 | Ranieri et al. | |
| 2002/0087206 A1 | 7/2002 | Hirschberg | |
| 2002/0146817 A1 | 10/2002 | Cannon et al. | |
| 2002/0187935 A1 * | 12/2002 | Redmond | A61F 9/008 514/100 |
| 2003/0100934 A1 | 5/2003 | Stephens et al. | |
| 2003/0185870 A1 | 10/2003 | Grinstaff et al. | |
| 2005/0038471 A1 | 2/2005 | Chan et al. | |
| 2005/0095235 A1 | 5/2005 | Austin et al. | |
| 2006/0212070 A1 | 9/2006 | Redmond | |
| 2006/0253176 A1 * | 11/2006 | Caruso | A61B 18/203 607/88 |
| 2007/0073364 A1 | 3/2007 | Meissner | |
| 2008/0009901 A1 | 1/2008 | Redmond et al. | |
| 2008/0139694 A1 | 6/2008 | Ratcliffe | |
| 2009/0287313 A1 | 11/2009 | Lowinger et al. | |
| 2010/0286475 A1 * | 11/2010 | Robertson | A61B 1/00096 600/104 |
| 2011/0152898 A1 | 6/2011 | Kochevar et al. | |
| 2012/0004499 A1 | 1/2012 | Ott | |
| 2012/0053419 A1 * | 3/2012 | Bloom | A61M 25/0013 600/146 |
| 2012/0209051 A1 | 8/2012 | Blumenkranz et al. | |
| 2013/0011753 A1 | 1/2013 | Genovesi | |
| 2013/0017532 A1 | 1/2013 | Genovesi | |
| 2013/0158515 A1 | 6/2013 | Austen, Jr. | |
| 2014/0217649 A1 | 8/2014 | Kochevar et al. | |
| 2015/0217025 A1 | 8/2015 | Hedman | |

FOREIGN PATENT DOCUMENTS

| | | |
|---|---|---|
| JP | 11-514869 A | 12/1999 |
| JP | 2004-510431 A | 4/2004 |
| JP | 2005-531336 A | 10/2005 |
| JP | 2007-90078 A | 12/2007 |
| WO | WO 97/13849 A1 | 4/1997 |
| WO | 1999065536 A1 | 12/1999 |
| WO | 00/07515 A1 | 2/2000 |
| WO | WO 02/28996 A1 | 4/2002 |
| WO | 03/084601 A2 | 10/2003 |
| WO | WO 2009/044407 A1 | 4/2009 |
| WO | WO 2010/051636 A1 | 5/2010 |
| WO | 2010062769 A1 | 6/2010 |
| WO | WO 2011082295 A2 | 7/2011 |
| WO | 2014015274 A9 | 1/2014 |

OTHER PUBLICATIONS

Chiniwala, et al., "Degenerative Tear of Tendo Achilles: Treatment by Primary Lengthening and Resuturing," Original/Research Articles, (Mar. 2010).

Bass, et al., "Laser Tissue Welding: A Comprehensive Review of Current and Future Clinical Applications," Lasers in Surgery and Medicine 17:315-349 (1995).

F. Saunders, "Tissue Welding," Science News (Jan. 1998).

Judy, et al., "Heat-free Photochemical Tissue Welding with 1,8-naphthalimide dyes using visible (420 nm) light," Baylor Research Institute Spie vol. 1876/175 (1993).

Salinas, H. M., et al., "Photochemical Tissue Passivation for Prevention of Vein Graft Intimal Hyperplasia", Plastic and Reconstructive Surgery, vol. 133, No. 3 (Mar. 2014).

Y. Chang, et al., "Cell-free Xenogenic Vascular Grafts Fixed with Glutaraldehyde or Genipin: In vitro and in vivo studies," J. Biotechnol. 120:207-19. (2005).

Y. Chang, et al., "Reconstruction of the right Ventricular Outflow Tract with a Bovine Jugular Vein Graft Fixed with a naturally occuring crosslinking agent (genipin) in a Canine Model," J. Thorac Cardiovasc Surg. 122:1208-18 (2001).

J. Fernandes, R.M.D., et al., "Prevention of Capsular Contracture with Photochemical Tissue Passivation," Plastic Reconstruction Surgery 133:571-7 (Mar. 2014).

P. F. Gratzer, et al., "Control of pH alters the Type of Cross-linking Produced by 1-ethyl-3-(3-dimethylaminopropyl)-carbodiimide (EDC) treatment of Acellular Matrix Vascular Grafts," Journal of Biomedical Materials Research 58(2):172-179 (2001).

Hsing-Wen Sung, et al., "Stability of a Biological Tissue Fixed with a Naturally Occuring Crosslinking Agent (genipin)," Journal of Biomedical Material Research 55(4):538-546 (2001).

H. M. Powell, et al., "EDC Cross-linking Improves Skin Substitute Strength and Stability," Biomaterials 27(34):5821-7 (2006).

Examination Report, Australian Patent Application No. 2014290513, dated Mar. 23, 2017.

Extended European Search Report, European Patent Application No. 14826821-2, dated Apr. 4, 2017.

A. C. Devkota et al., "A Tissue Explant System for Assessing Tendon Overuse Injury" Department of Biomedical Engineering, 1350-4533, 2004.

International Search Report issued in PCT/US2014/047146 dated Nov. 26, 2014.

(56) References Cited

OTHER PUBLICATIONS

Written Opinion issued in PCT/US2014/047146 dated Nov. 26, 2014.
International Search Report and Written Opinion, International Patent Application No. PCT/US2013/051333, dated Nov. 7, 2013.
Communication Pursuant to Rule 164(1) EPC, European Patent Application No. 14826821.2, dated Nov. 30, 2016.
Office Action, U.S. Appl. No. 14/601,023, dated May 2, 2016.
Office Action, U.S. Appl. No. 14/601,023, dated Sep. 6, 2016.
Office Action, U.S. Appl. No. 14/601,023, dated Dec. 23, 2016.
Ng-Glazier, J. et al., "A Photochemical Tissue Bonding Approach for Sutureles Microvascular Anastamosis in an Arterial Graft Model", Plastic & Reconstructive Surgery: vol. 133—Issue 33, Mar. 2014.
Office Action, U.S. Appl. No. 14/601,023, dated Jun. 14, 2017.
Examination Report No. 1, Australian Patent Application No. 2014233300, dated Dec. 12, 2017.
Office Action, U.S. Appl. No. 14/601,023, dated Jan. 9, 2018.
Examination Report No. 1 for your standard patent application, Australian Patent Application No. 2017210560, dated May 29, 2018.
Communication Pursuant to Article 94(3) EPC, European Patent Application No. 14826821.2, dated Mar. 23, 2018.
Office Action, Japanese Patent Application No. 2016-527118, dated Jan. 31, 2017.
Office Action, Japanese Patent Application No. 2017-125368, dated Jun. 26, 2018.
Communication—Extended European Search Report, European Patent Application No. 14 762 268.2, dated Oct. 28, 2016.
Communication pursuant to Article 94(3) EPC, European Patent Application No. 14 826 821.2-1454, dated Dec. 15, 2017.
Communication pursuant to Article 94(3) EPC, European Patent Application No. 14 762 268.2, dated Mar. 6, 2018.
Office Action, U.S. Appl. No. 14/601,023, filed Sep. 27, 2018.
Heiting, G. et al., Sclera: The White of the Eye, https://www.allaboutvision.com/resources/sclera.htm, downloaded Sep. 20, 2018.
Schmidt, M. H. et al., Light-emitting Diodes as a Light Source for Intraoperative Photodynamic Therapy, Neurosurgery, vol. 38, No. 3, Mar. 1996.
International Search Report and Written Opinion, International Patent Application No. PCT/US2014/047146, dated Nov. 26, 2014.
Office Action, U.S. Appl. No. 14/849,266, dated Nov. 29, 2018.
Office Action, Japanese Patent Application No. 2016-503273, dated Jan. 9, 2018.
Office Action, Japanese Patent Application No. 2016-503273, dated Sep. 11, 2018.
Advisory Action, Japanese Patent Application No. JP2017-125368, dated Jan. 22, 2019.

\* cited by examiner

VESSEL TREATMENT SYSTEMS, METHODS, AND KITS

CROSS-REFERENCE TO RELATED APPLICATIONS

This application is a continuation under 35 U.S.C. § 120 of International Application No. PCT/US2014/047146, filed Jul. 18, 2014, which claims priority to U.S. Provisional Patent Application Ser. No. 61/847,794, filed Jul. 18, 2013. This application also contains subject matter that may be related to U.S. Provisional Patent Application Ser. Nos. 61/674,235 and 61/784,708, filed Jul. 20, 2012 and Mar. 14, 2013, respectively, and International Application No. PCT/US2013/051333, filed Jul. 19, 2013. The entire disclosures of each of the aforementioned applications are incorporated herein by reference.

STATEMENT REGARDING FEDERALLY SPONSORED RESEARCH OR DEVELOPMENT

This invention was made with government support under Grant No. FA9550-11-1-0331 awarded by the Air Force Office of Scientific Research. The Government has certain rights in this invention.

BACKGROUND

Grafting of blood vessels using sections of veins can be used to correct or treat a variety of conditions. For example, vein segments taken from a non-critical part of the body (such as the great saphenous vein in the leg) can be used to replace segments of damaged or diseased blood vessels (arteries or veins) in other parts of the body, such as in certain coronary bypass procedures or to treat peripheral vascular disease. A vein in the arm can also be joined directly to a nearby artery through an anastomosis to create an arteriovenous fistula, which can facilitate vascular access in patients that require hemodialysis treatments.

Vein grafts and arteriovenous fistulas have poor long-term patency rates, which may be due to factors such as luminal narrowing that results from intimal hyperplasia, medial thickening, and subsequent superimposed accelerated atherosclerosis. Intimal hyperplasia can result from the intimal injury that ensues after excessive stretching of the vein graft as it is exposed to arterial pressure.

SUMMARY OF THE INVENTION

Exemplary embodiments of the present disclosure provide a method and apparatus for treating a segment of vein or other vessel using phototherapy to strengthen and/or stiffen the outer surface of the vessel and improve patency thereof. The apparatus includes a mounting arrangement configured to secure at least a portion of the vessel in an appropriate environment, an applicator arrangement adapted to spray or otherwise infuse a surface portion of the vessel tissue with a passivation agent (such as Rose Bengal), and an optional light-emitting arrangement capable of uniformly and controllably irradiating the tissue surfaces to activate a photoactive agent and improve properties of the vessel tissue.

The apparatus can be used ex vivo to treat certain segments of vein graft material removed from the body prior to their grafting into another portion of the body. In certain embodiments, the method and apparatus can be used to treat the venous portion of an arteriovenous fistula or the like during the procedure in a patient's body.

These and other objects, features and advantages of the present disclosure will become apparent upon reading the following detailed description of exemplary embodiments of the disclosure, when taken in conjunction with the appended exemplary figures.

One aspect of the invention provides a vessel treatment system including: a housing defining at least one opening adapted and configured to receive an anatomical vessel; and a humidifier in communication with the housing, the humidifier adapted and configured to introduce humidity into the housing to prevent desiccation of the anatomical vessel.

This aspect of the invention can have a variety of embodiments. For example, the system can further include: an applicator adapted and configured to apply a passivation agent to the anatomical vessel. The applicator can further include one or more selected from the group consisting of: a nozzle, a mister, a brush, and a drip orifice. The system can further include a passivation agent reservoir in fluid communication with the applicator.

The system can further include a light emitter adapted and configured to generate light of a sufficient wavelength to induce a chemiluminescent reaction in a passivation agent. The sufficient wavelength can be between about 400 nm and about 700 nm. The sufficient wavelength can be about 532 nm. The sufficient wavelength can be between about 700 nm and about 1,000 nm.

The system can further include one or more reflectors adapted and configured to reflect the light generated by the light emitter within the housing. The system can include one or more shields adapted and configured to substantially confine the light generated by the light emitter within the housing.

The humidifier can further include one or more selected from the group consisting of: a standing volume of water within the housing, a nozzle, a mister, a vaporizer, an ultrasonic humidifier, and a drip orifice. The humidifier can include a vessel of humidified air.

The system can further include a rotor adapted and configured to rotate the anatomical vessel within the housing. The rotor can be adapted and configured to rotate the blood vessel at a speed between about 30 revolutions per minute and about 120 revolutions per minute. The rotor can be selected from the group consisting of: an electrical motor, a pneumatic rotor, and a hydraulic rotor.

The system can further include a clamp adapted and configured to releasably grip the anatomical vessel.

The system can further include a controller programmed to control operation of one or more components of the vessel treatment system.

At least one of the at least one opening can have a concave profile substantially complimentary to a palmar surface of a human forearm. At least one of the at least one opening can include a gasket adapted form a substantially airtight seal against human skin.

Another aspect of the invention provides a vessel treatment system including: a housing defining at least opening adapted and configured to receive an anatomical vessel; a humidifier adapted and configured to prevent desiccation of the anatomical vessel; a light emitter adapted and configured to generate light of a sufficient wavelength to induce a chemiluminescent reaction within a photoactive passivation agent applied to an exterior surface of the anatomical vessel; a rotor adapted and configured to rotate the anatomical vessel within the housing; and a controller programmed to control operation of one or more components of the vessel treatment system to apply a specified amount of fluence to the photoactive passivation agent.

Another aspect of the invention provides a kit including: the vessel treatment system as described herein; and a passivation agent.

This aspect of the invention can have a variety of embodiments. The passivation agent can include Rose Bengal, toluidine blue, riboflavin, Genipin, or EDC. The kit can further include instructions for use.

Another aspect of the invention provides a method for preparing a vein graft. The method includes: applying a tissue passivation agent to a resected anatomical vessel; and placing the resected anatomical vessel in a humidified chamber while the tissue passivation agent cures.

This aspect of the invention can have a variety of embodiments. The tissue passivation agent can be a photoactive cross-linker and the method can further include applying light at a suitable wavelength to cure the photoactive across-linker. The tissue passivation agent can be a chemical cross-linker. The resected blood vessel can remain attached to a subject's body by one end and the humidified chamber can form a seal against subject's skin.

BRIEF DESCRIPTION OF THE DRAWINGS

For a fuller understanding of the nature and desired objects of the present invention, reference is made to the following detailed description taken in conjunction with the accompanying drawing figures wherein like reference characters denote corresponding parts throughout the several views and wherein.

DEFINITIONS

The instant invention is most clearly understood with reference to the following definitions.

As used herein, the singular form "a," "an," and "the" include plural references unless the context clearly dictates otherwise.

Unless specifically stated or obvious from context, as used herein, the term "about" is understood as within a range of normal tolerance in the art, for example within 2 standard deviations of the mean. "About" can be understood as within 10%, 9%, 8%, 7%, 6%, 5%, 4%, 3%, 2%, 1%, 0.5%, 0.1%, 0.05%, or 0.01% of the stated value. Unless otherwise clear from context, all numerical values provided herein are modified by the term about.

As used in the specification and claims, the terms "comprises," "comprising," "containing," "having," and the like can have the meaning ascribed to them in U.S. patent law and can mean "includes," "including," and the like.

Unless specifically stated or obvious from context, the term "or," as used herein, is understood to be inclusive.

Ranges provided herein are understood to be shorthand for all of the values within the range. For example, a range of 1 to 50 is understood to include any number, combination of numbers, or sub-range from the group consisting 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 (as well as fractions thereof unless the context clearly dictates otherwise).

DETAILED DESCRIPTION OF THE INVENTION

Vessel Treatment Apparatuses

Figure 1:
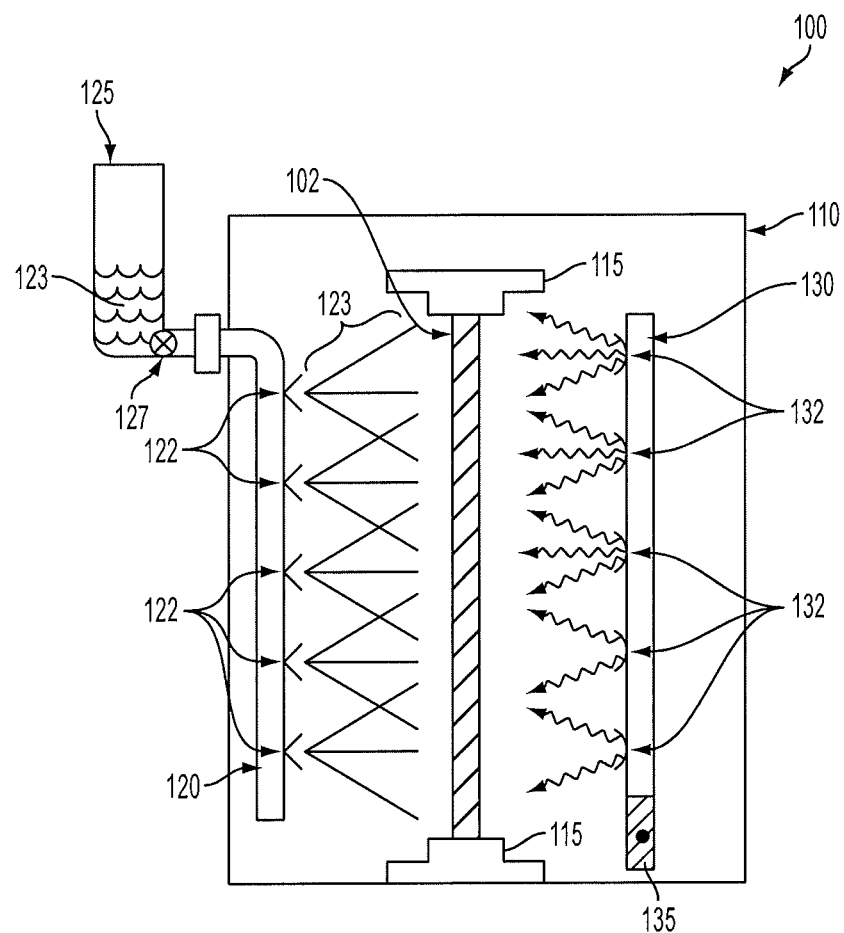
FIG. 1 depicts a vessel treatment apparatus according to an embodiment of the invention.

A vessel treatment apparatus 100 that can be used for treatment of ex vivo vein graft segments in accordance with exemplary embodiments of the present disclosure is shown in FIG. 1. The apparatus 100 can facilitate phototreatment of, e.g., a vein graft segment 102 to improve certain properties while avoiding damage to the tissue that could make it unsuitable for use as a graft.

The apparatus 100 includes an enclosed housing 110, shown in side view. The shape of the housing 110 can be rectangular, cylindrical, etc. The height of the housing 110 is preferably longer than the largest length of vein tissue 102 to be treated therein. For example, the housing 110 can have a height of between about 1 inch and 2 inches, between about 2 inches and about 3 inches, between about 3 inches and about 4 inches, between about 4 inches and about 5 inches, between about 5 inches and about 6 inches, between about 6 inches and about 7 inches, between about 7 inches and about 8 inches, between about 8 inches and about 9 inches, between about 9 inches and about 10 inches, between about 10 inches and about 11 inches, between about 11 inches and about 12 inches, between about 12 inches and about 13 inches, between about 13 inches and about 14 inches, between about 14 inches and about 15 inches, between about 15 inches and about 16 inches, between about 16 inches and about 17 inches, between about 17 inches and about 18 inches, and the like.

The apparatus 100 can further include a pair of clamps 115 (e.g., conventional vein clamps or the like) coupled to the housing 110 and adapted to hold the ends of the vein graft 102 without stretching it or applying any undesirable mechanical forces or stresses to it. The clamps 115 can also be configured to cover or protect the open ends of the vein graft 102, such that no passivation agent 123 or other foreign substance enters the lumen of the vein graft 102. In general, it may be preferable to avoid modifying or damaging the endothelium lining the inner surface of the vein graft 102, such that only external surfaces of the graft 102 are treated or modified by the apparatus 100.

The apparatus 100 can further includes one or more applicator arrangements 120. The applicator arrangement 120 is adapted and configured to spray, soak, or otherwise apply a liquid passivation agent 123 to the outer surface of the vein graft 102. For example, the applicator arrangement 120 can include a tube with a plurality of holes or nozzles 122 adapted and configured to direct a spray of passivation agent 123 onto the surface of the vein graft 102. The applicator arrangement 120 can include a reservoir 125 capable of holding a quantity of the passivation agent 123, and a controllable valve arrangement 127 adapted and configured to control the amount and/or duration of the applied passivation agent 123. The reservoir 125 can be maintained under pressure, e.g., as a sealed pressurized enclosure such that opening the valve arrangement 127 will cause the agent 123 to be emitted from the nozzles 122. The agent 123 an also be directed onto the vein graft 102 using a pressurized air or gas line, or a conventional pumping arrangement that can be coupled to the applicator arrangement 120 using conventional fittings or the like.

The apparatus 100 can further include one or more light-emitting arrangements 130 that are capable of uniformly and controllably irradiating the surface of the vein graft 102 with light having a particular fluence and one or more particular wavelengths, when the passivation agent 123 is a photoactive passivation agent. The light-emitting arrangement 130 can be provided with one or more light sources 132, such as light-emitting diodes (LEDs), laser diodes, or the like. The number and/or shape of such light sources 132 can be selected to provide substantially uniform fluence along the length of the vein graft 102 when in use. In certain embodiments, the light sources 132 can include reflectors and/or diffusers to improve the spatial uniformity of the emitted light. Portions of the interior surface of the housing 110 can also be made of or coated with a reflective material to facilitate uniform irradiation of the vein graft 102. Optionally, the light-emitting arrangement 130 can include one or more optical fibers or waveguides capable of directing light from an external source onto the vein graft 102.

The light-emitting arrangement 130 can be provided with a control arrangement 135 that can be used to control the operation of the light sources 132, e.g., by controlling the power supplied to the light sources 132 and/or controlling the duration that they are illuminated. A power source for the light-emitting arrangement 130 can be provided within or external to the housing 110. In certain embodiments, an external source of electricity can be used, and the apparatus 100 can be provided with a socket or receptacle to direct electricity from the external source to the light-emitting arrangement 130.

The interior of the housing 110 is preferably maintained in a humid state to avoid excessive desiccation of the vein graft 102 during treatment. This can be achieved by flowing or injecting a mist of water or saline into the interior of the housing 110. For example, a humidifying arrangement can be provided that is similar to the applicator arrangements 120, but adapted to spray saline instead of the passivation agent 123. Saline can also be introduced into the housing 110 from an external source via one or more ports provided in the housing 110, by an ultrasonic vaporizer provided within the housing 110, and the like The apparatus 100 shown in FIG. 1 is an illustration of an exemplary configuration, and other embodiments using various combinations and/or configurations of similar components can also be used. For example, 2, 3, or more the applicator arrangements 120 can be provided within the housing 110 in various orientations to improve the uniformity of the application of the passivation agent 123 to the graft surface. Similarly, a plurality of light-emitting arrangements 130 can be provided to facilitate uniform irradiation of the entire graft surface. In certain embodiments, the vein clamps 115 can be controllably rotatable, e.g., using a motor-driven arrangement, such that the vein graft 102 can be rotated during application of the agent 123 and/or light to improve surface uniformity of the graft treatment procedure.

In further embodiments, the vein graft 102 can be mounted in a horizontal orientation rather than the exemplary vertical orientation shown in FIG. 1, or at any other angle. A plurality of pairs of clamps 115 can also be provided in a single housing 110 to facilitate treatment of a plurality of vein grafts 102 at the same time in a single apparatus 100.

In further embodiments, the applicator arrangement 120 can be external to the housing 110, e.g., coupled to an exterior surface of the housing 110, such that the passivation agent 123 is directed through one or more nozzles or holes 122 that pass through the walls of the housing 110 and onto the vein graft 102 within the enclosed volume. Similarly, light-emitting arrangement 130 can be provided exterior to the housing 110, e.g., such that light can be directed onto the vein graft 102 through optically transparent portions of the housing 110. Providing certain arrangements external to the housing 110 in this manner can simplify the configuration of the housing 110 itself, which can facilitate its sterilization for re-use, or enable parts of the apparatus 100 (e.g. housing 110 and clamps 115) to be single-use or disposable.

In operation, a vein graft 102 removed from a subject can be affixed to the clamps 115 and held within the housing 110, as shown in FIG. 1. The interior of the housing 110 can be maintained in a humidified state, as described herein. The vein graft 102 can be covered uniformly with an amount of the passivation agent 123 using the applicator arrangement 120. The passivation agent 123 can be allowed to interact with the vein graft 102 for sufficient time to allow sufficient absorption prior to implantation and/or effective treatment of the vein graft 102 with light if a photoactive passivation agent is used. For example, a duration of about 30 seconds or more can be sufficient time for a solution of Rose Bengal to remain on the vein graft 102 before subsequent irradiation with light.

If a photoactive passivation agent is used, the light-emitting arrangement 130 can then be activated for a particular duration and at a particular power or intensity level to irradiate the vein graft 102. The control arrangement 135 can be configured to control the duration, timing, intensity and/or other parameters of the light provided by the light-emitting arrangement 130. For example, light-emitting arrangement 130 can be configured to emit light at a single intensity, and variation in the total fluence irradiating the graft 102 can be controlled by varying the duration that the light-emitting arrangement 130 is activated. In certain embodiments, the light-emitting arrangement 130 can be activated intermittently (e.g. as a series of short or long pulses) to avoid excessive heating of the vein graft 102, based on such factors as the type of light sources 132 used and the size of the enclosure 110. The duration of irradiation of the vein graft 102 can be typically on the order of several minutes, although shorter or longer durations may be preferable based on such factors as the type and number of light sources 132, the size of the vein graft 102, the distance between the light sources 132 and the vein graft 102, the characteristics of the emitted light and the particular passivation agent 132 used, and the like.

After treatment, the vein graft 102 can be removed from the apparatus 100 and grafted into a patient. The ends of the vein graft 102 held within the clamps 115 can be cut off if these ends are not exposed to the passivation agent 123 and light, to avoid producing a graft with untreated end regions. The phototreated vein graft 102 can have stronger material properties than the original vein, such that it can better contain the higher arterial pressure it may be exposed to when implanted.

Figure 2:
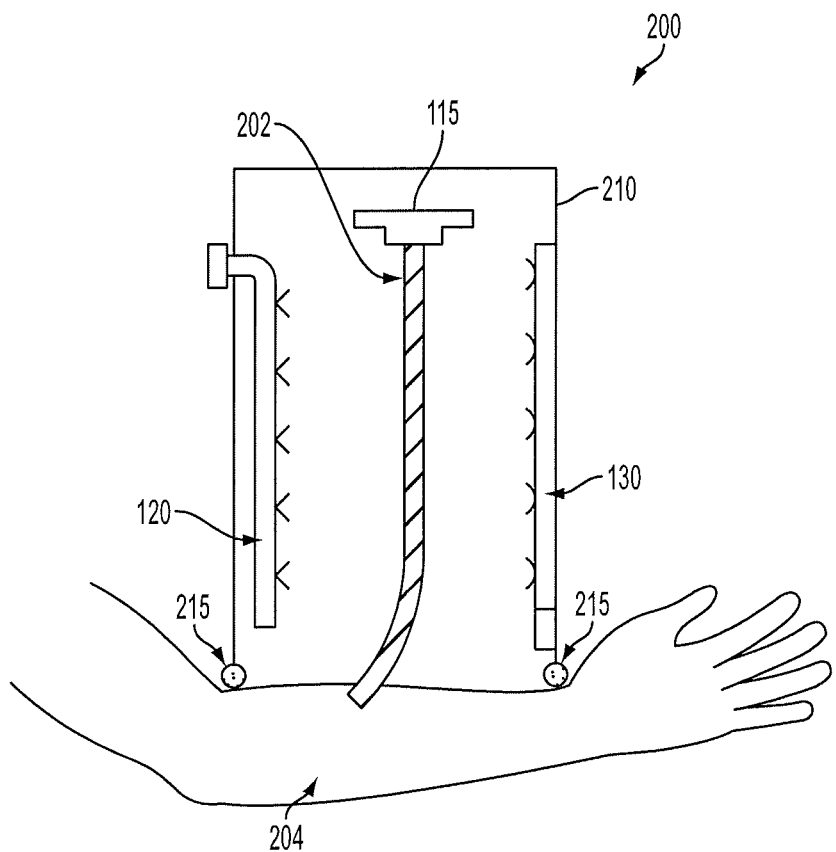
FIG. 2 depicts an apparatus for treating vein segments used to form arteriovenous fistulas according to an embodiment of the invention.

In further embodiments, an apparatus and method for treating vein segments used to form arteriovenous fistulas and the like can be provided, as shown in FIG. 2. Unlike the vein graft 102 treated by the apparatus 100 in FIG. 1, the vein segment 202 used to form the fistula is not fully removed from the body. Instead, the vein segment 202 (often located in the forearm 204 of a patient) remains attached to the body, with one end thereof being cut and then connected to a nearby artery to form the fistula.

The lower portion of the housing 210 of the apparatus 200 can be at least partially open, to allow the severed end of the vein segment 202 to be directed into the interior of the housing 210 and affixed to a vein clamp 115. A lower clamp, spacer, or the like can be provided to stabilize the lower end of the vein segment 202 where it enters the apparatus 200. The bottom of the housing 210 can be shaped to contact the arm 204 of the patient. A seal 215 (e.g., a flexible material) can be provided on the lower edges of the housing 210 to improve contact of the housing 210 with the arm 204, e.g., to help enclose the interior volume of the housing 210 during the procedure.

The apparatus 200 includes one or more applicator arrangements 120 and light-emitting arrangements 130, which can be provided with components and configurations similar to those described with respect to apparatus 100 above. For clarity, exemplary details of these arrangements are not shown in FIG. 2. A humidifying arrangement can also be provided to maintain a hydrated environment for the vein segment 202 during treatment.

The apparatus 200 can be used to improve the strength and patency of the vein segment 202 used to form an arteriovenous fistula. A vein segment 202 that will form the fistula can be separated from the arm 204 and affixed to the clamp 115 within the housing 110, as shown in FIG. 2. The apparatus 200 can be used to apply a passivation agent to the vein segment 202, as described above, and, in the case of a photoactive agent, the vein segment 202 can then be irradiated using light-emitting arrangement 130. The lower portion of the housing 210 can optionally be structured to catch excess agent 123 and/or prevent it from entering the incision created in the arm 204 to extract the vein segment 202. The total time for this in situ treatment process can be on the order of a few minutes or more, and may thus be sufficiently brief to not present a significant interruption of the fistula procedure. After treatment, the apparatus 200 can be removed, and the strengthened vein segment 202 can be used to form the fistula. The end of the vein segment 202 that is held within the clamp 115 can optionally be cut off such that the resulting end of the vein segment 202 (which can then be attached to an artery) is fully treated and strengthened, which can improve the suture-retaining properties thereof.

Figure 3:
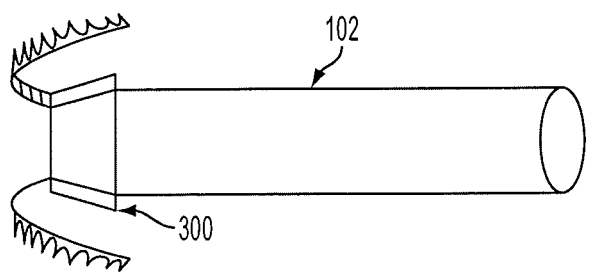
FIG. 3 depicts a collar arrangement for treating an interior surface of an anatomical vessel.

In a further embodiment, the interior surface of the end portions of a vein graft 102 can be treated as described herein to further improve the strength or other properties of the end region (which may be sutured). Although it may be undesirable to treat or affect the inner surface of the vein lumen along its length, the end portions thereof can be treated using an exemplary collar arrangement 300 as shown in FIG. 3. The collar arrangement 300 can be placed over the end region of a vein graft 102, and the end of the vein graft 102 can then be inverted over the collar arrangement 300, as shown in FIG. 3, to expose a short end portion of the inside surface of the vein graft 102.

An apparatus such as the phototreatment apparatus 100, 200 shown in FIGS. 1 and 2, respectively, can be used to apply the passivation agent 123 to the end portion of the vein graft 102 and then irradiate it, if necessary, as described above. The clamp 115 can be adapted to secure the end region of the vein graft 102, e.g., by providing a protrusion shaped to be inserted into the lumen of the vein graft 102 within the collar 300 to hold the vein graft 102 during phototreatment. An open clamp structure can also be provided that couples directly to the collar 300 while not obstructing the exposed inner surface of the graft end. In further embodiments, a passivation agent 123 and optionally light can be applied manually to the exposed inside end of the vein graft 102.

Figure 4:
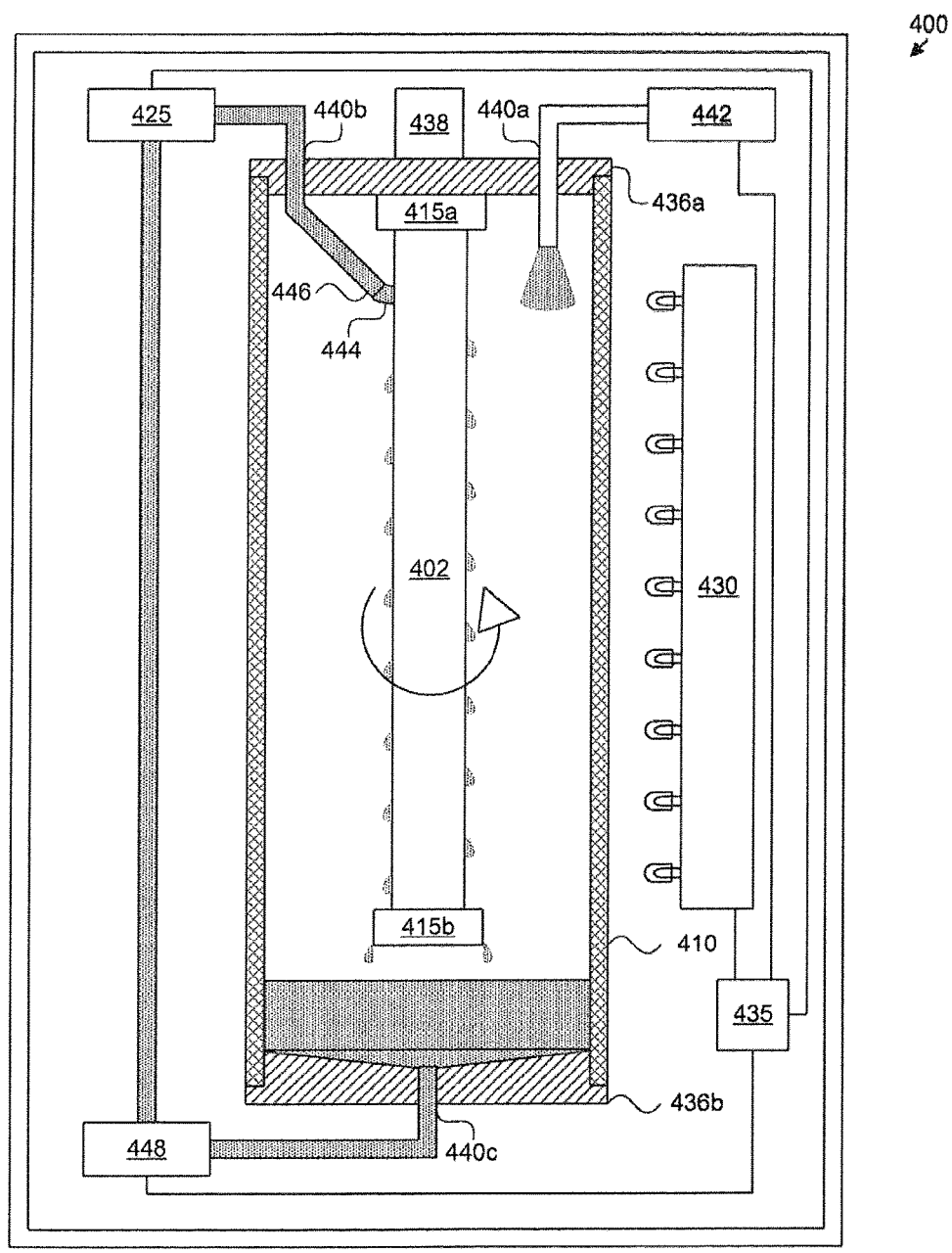
FIG. 4 depicts a vessel treatment apparatus according to an embodiment of the invention.

Referring now to FIG. 4, another embodiment of a vessel treatment system 400 is provided. System 400 can include a vessel housing 410 adapted and configured to receive a blood vessel 402. Housing 410 can be adapted and configured to isolate the blood vessel 402 and any liquids applied thereto from some or all the other components of the system 400 so that some or all of the components of the system 400 can be reused without the need for sterilization and so that housing 410 and related components can be sterilized without harming other components of system 400.

Housing 410 can be fabricated from a material that is substantially optically transparent at a wavelength of interest (e.g., between about 400 nm and about 700 nm, about 532 nm, between about 700 nm and about 1,000 nm, and the like). Suitable materials include glass or acrylic glass (polymethyl methacrylate or PMMA). Acrylic glass is available under the LUCITE® and PERSPEX® trademarks from Lucite International, Inc. of Cordova, Tenn.

Housing 410 can be sealed by caps 436a, 436b to provide a substantially air and fluid tight seal over the course of a typical procedure (e.g., up to about 10, about 15, about 20, about 25, and about 30 minutes). Caps can be formed or include an elastomeric material in order to form a compressive seal. Additionally or alternatively, caps 436 can be threaded into complimentary threads in housing 410.

One or more clamps 415a, 415b can hold blood vessel 402 within housing 410. In one embodiment, a top clamp 415a is coupled to the top cap 436a. Bottom clamp 415b can be coupled to bottom cap 436b or can be unattached and instead, simply provide slight tension to blood vessel 402 while rotating freely as blood vessel 402 rotates.

A rotor 438 can clamp 415a (and thereby blood vessel 402) in order to provide even application of a passivation agent and/or light to the blood vessel 402. Rotation can be translated across top cap 436a by a variety of means such as a stud extending from clamp 415a through the top cap 436a or by magnetic coupling across top cap 436a.

Caps 436 can include one or more orifices to permit inflow and outflow of one or more fluids from housing 410. For example, orifice 440a can receive humidified air or water from a humidifier 442. Orifice 440b can receive a passivation agent 444 from a reservoir 425. Passivation agent 444 can be applied through a variety of means such as nozzles, misters, brushes, drip orifices, and the like. For example, as depicted in FIG. 4, passivation agent 444 can be wicked from drip orifice 446 onto either blood vessel 402 or clamp 415 as the blood vessel 402 or claim 415 rotates and can flow down blood vessel 402 due to gravity.

In some embodiments, sufficient quantities of the passivation agent 444 can be applied blood vessel 402, so that passivation agent 444 and/or associated reservoir 425 and/or pump 448 function as a humidifier to prevent desiccation of the blood vessel 402. This is particularly true when the passivation agent 444 is an aqueous solution.

Excess passivation agent 444 and/or water can be collected from the bottom of the housing 410 via orifice 440c and recirculated via reservoir 425 and/or pump 448.

A control unit 435 can be programmed to control the operation of rotor 438, pump 448, reservoir 448, light-emitting arrangement 430, and/humidifier to prevent desiccation of blood vessel, apply an appropriate amount of passivation agent 444 to the blood vessel 402, apply an appropriate amount of light to the blood vessel 402 after application of the passivation agent 444, and/or otherwise implement all or parts of the methods described herein.

Control unit 435 can be an electronic device programmed to control the operation of the system 400 to achieve a desired result. The control unit 435 can be programmed to autonomously carry out a method for preparing and/or preserving a vein graft without the need for input (either from feedback devices or medical professionals) or can incorporate such inputs.

Control unit 435 can be a computing device such as a general purpose computer (e.g., a personal computer or PC), workstation, mainframe computer system, and so forth. Control unit 435 can include a processor device (or central processing unit "CPU"), a memory device, a storage device, a user interface, a system bus, and/or a communication interface.

A processor can be any type of processing device for carrying out instructions, processing data, and so forth.

A memory device can be any type of memory device including any one or more of random access memory ("RAM"), read-only memory ("ROM"), Flash memory, Electrically Erasable Programmable Read Only Memory ("EEPROM"), and so forth.

A storage device can be any data storage device for reading/writing from/to any removable and/or integrated optical, magnetic, and/or optical-magneto storage medium, and the like (e.g., a hard disk, a compact disc-read-only memory "CD-ROM", CD-ReWritable "CD-RW", Digital Versatile Disc-ROM "DVD-ROM", DVD-RW, and so forth). The storage device can also include a controller/interface for connecting to a system bus. Thus, the memory device and the storage device can be suitable for storing data as well as instructions for programmed processes for execution on a processor.

The user interface can include a touch screen, control panel, keyboard, keypad, display or any other type of interface, which can be connected to a system bus through a corresponding input/output device interface/adapter.

The communication interface can be adapted and configured to communicate with any type of external device. The communication interface can further be adapted and configured to communicate with any system or network, such as one or more computing devices on a local area network ("LAN"), wide area network ("WAN"), the Internet, and so forth. The communication interface can be connected directly to a system bus or can be connected through a suitable interface.

The control unit 435 can, thus, provide for executing processes, by itself and/or in cooperation with one or more additional devices, that can include algorithms for controlling various components of the systems 100, 200, 400 in accordance with the present invention. Control unit 435 can be programmed or instructed to perform these processes according to any communication protocol and/or programming language on any platform. Thus, the processes can be embodied in data as well as instructions stored in a memory device and/or storage device or received at a user interface and/or communication interface for execution on a processor.

The control unit 435 can control the operation of the system components in a variety of ways. For example, control unit 435 can modulate the level of electricity a component. Alternatively, the control unit 435 can transmit instructions and/or parameters a system component for implementation by the system component.

Control unit 435 can interface with one or more feedback devices in order to monitor operation of the systems 100, 200, 400. For example, one or more feedback devices can provide information regarding the temperature and/or humidity within the housing, an elapsed time since the blood vessel 402 was received within the system 400, and/or the amount light applied by the light-emitting arrangements 130, 430.

System 400 can be completely or partially surrounded by a shell 450. Shell 450 can be adapted and configured to maintain reflect light within the system 400 and/or prevent potentially harmful energy from escaping the system 400, which would necessitate certain precautions such as protective eyewear when the system 400 is utilized. In some embodiments, shell 450 is opaque to the wavelength of interest and/or bears a reflective coating.

Methods of Treating a Vessel

Figure 5:
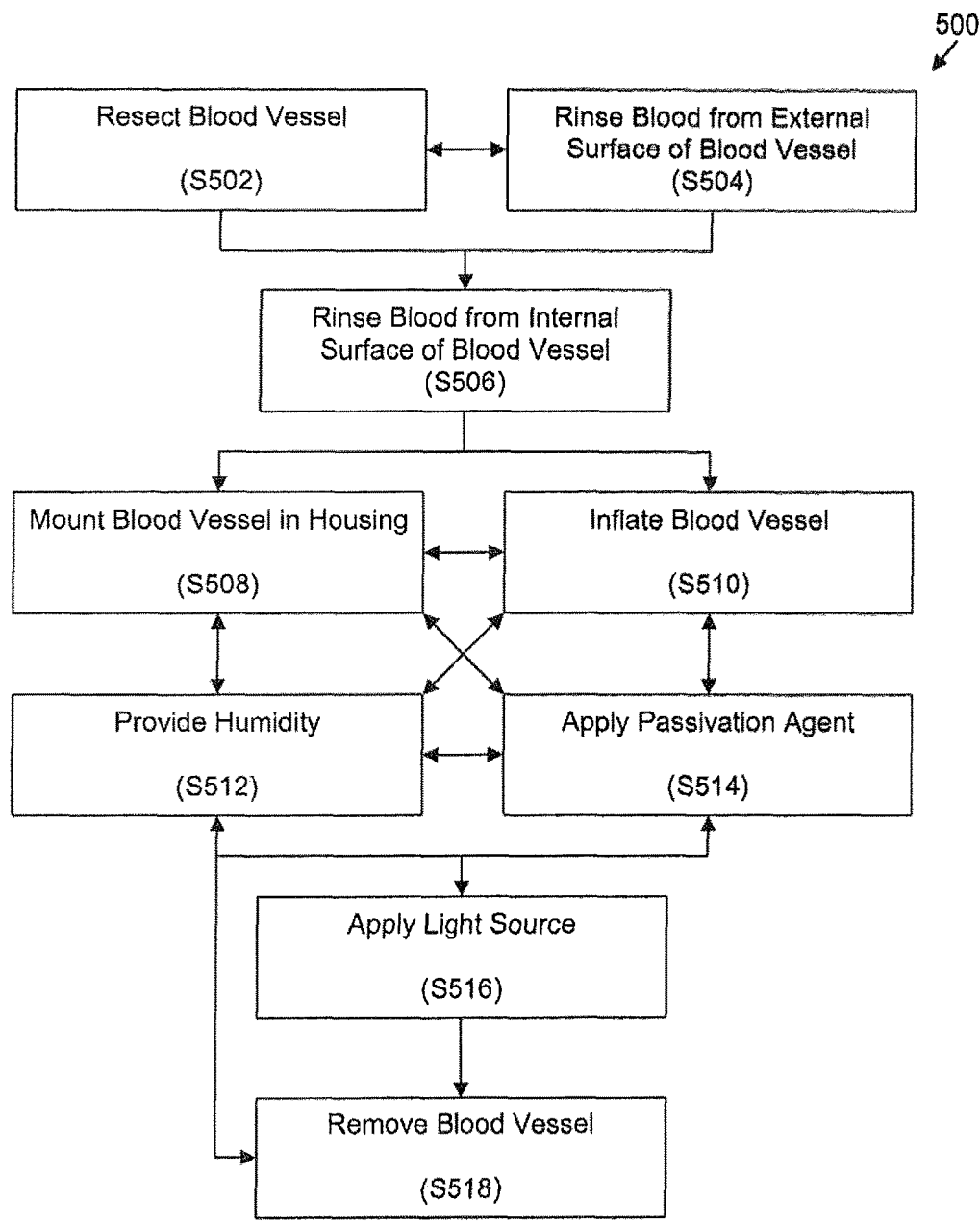
FIG. 5 depicts a method of treating a vessel according to an embodiment of the invention.

Referring now to FIG. 5, a method 500 of treating a vessel is provided. In step S502, a blood vessel is resected from a subject's body, e.g., in accordance with standard surgical techniques. In step S504, blood is rinsed from the external surface of the blood vessel. Steps S502 and S504 can be performed in parallel as the blood vessel is resected in order to prevent coagulation of blood on the blood vessel. In step S506, blood is rinsed from the internal surface of the blood vessel. Rinsing can be performed using water, saline solution, heparinized saline solution, another biocompatible fluid, and the like.

In step S508, the resected and rinsed blood vessel is mounted in a housing (e.g., with clamps). In step S510, the blood vessel can be pressurized, for example, by filling the vessel with a fluid such as saline solutions, heparinized saline solution, another biocompatible fluid, and the like. Such an inflation fluid can be introduced using an angiocatheter, a cannula, and the like and can be retained using clamps as described herein. Blood vessel can be inflated to a pressure found within normal anatomical conditions. For example, blood vessel can be pressurized to about 150 mm Hg.

In another embodiment, blood vessel can be inflated by pressurized fluid flow while in the housing. In such an embodiment, hose clamps, bands, or sutures can be used to couple the blood vessel to a tube or fitting. Light-emitting arrangements can surround the housing or can be rotated around a stationary housing to provide uniform light exposure.

In step S512, humidity is applied to the blood vessel. In step S514, a passivation agent is applied to the blood vessel. In step S516, a light source is applied to activate the passivation agent. The intensity and/or duration of light can be controlled to generate a desired amount of fluence. For example, light can be controlled to generate a fluence of between about 5 $J/cm^2$ and about 10 $J/cm^2$, between about 10 $J/cm^2$ and about 15 $J/cm^2$, between about 15 $J/cm^2$ and about 20 $J/cm^2$, between about 20 $J/cm^2$ and about 25 $J/cm^2$, between about 25 $J/cm^2$ and about 30 $J/cm^2$, between about 30 $J/cm^2$ and about 35 $J/cm^2$, between about 35 $J/cm^2$ and about 40 $J/cm^2$, between about 40 $J/cm^2$ and about 45 $J/cm^2$, between about 45 $J/cm^2$ and about 50 $J/cm^2$, between about 50 $J/cm^2$ and about 55 $J/cm^2$, between about 55 $J/cm^2$ and about 60 $J/cm^2$, between about 60 $J/cm^2$ and about 65 $J/cm^2$, between about 65 $J/cm^2$ and about 70 $J/cm^2$, between about 70 $J/cm^2$ and about 75 $J/cm^2$, between about 75 $J/cm^2$ and about 80 $J/cm^2$, between about 80 $J/cm^2$ and about 85 $J/cm^2$, between about 85 $J/cm^2$ and about 90 $J/cm^2$, between about 90 $J/cm^2$ and about 95 $J/cm^2$, between about 95 $J/cm^2$ and about 100 $J/cm^2$, and the like.

Passivation Agents

The passivation agents discussed herein can include one or more biocompatible cross-linkers, protein cross-linkers, collagen cross-linkers, and the like.

Suitable cross-linkers include photoactive cross-linkers such as Rose Bengal (4,5,6,7-tetrachloro-3',6'-dihydroxy-2',4',5',7'-tetraiodo-3H-spiro[isobenzofuran-1,9'-xanthen]-3-one), which is activated by a wavelength of about 525 nm; toluidiene blue (tolonium chloride), which is activated by infrared light; and riboflavin (7,8-dimethyl-10-[(2S,3S,4R)-2,3,4,5-tetrahydroxypentyl]benzo[g]pteridine-2,4-dione), which is activated by blue light.

Suitable chemical cross-linkers include Genipin (methyl 1R,2R,6S)-2-hydroxy-9-(hydroxymethyl)-3-oxabicyclo[4.3.0]nona-4,8-diene-5-carboxylate) and EDC (1-ethyl-3-(3-dimethylaminopropyl)carbodiimide). Chemical cross-linkers do not require photoactivation to cure and, instead, cure within minutes (e.g., about 10 minutes) after application to a vessel.

EQUIVALENTS

The foregoing merely illustrates the principles of the disclosure. Various modifications and alterations to the described embodiments will be apparent to those skilled in the art in view of the teachings herein. It will thus be appreciated that those skilled in the art will be able to devise numerous techniques and variations which, although not explicitly described herein, embody the principles of the disclosure and are thus within the spirit and scope of the disclosure.

For example, although aspects of the invention were described in the context of blood vessels, aspect of the invention can be applied to other anatomical vessels such as skin, scar tissue, cartilage, tendons, ligaments, and the like.

Likewise, although aspects of the invention depict systems and methods that operate on single blood vessels, such systems and methods can easily be modified to treat a plurality of blood vessels (e.g., 2, 3, 4, 5, 6, 7, 8, 9, 10, and the like) in parallel.

INCORPORATION BY REFERENCE

The entire contents of all patents, published patent applications, and other references cited herein are hereby expressly incorporated herein in their entireties by reference.

The invention claimed is:

1. A method for preparing a vein graft, the method comprising:
   applying a tissue passivation agent to a resected anatomical vessel;
   placing the resected anatomical vessel in a humidified chamber, wherein the resected blood vessel remains attached to a subject's body by one end and the humidified chamber forms a seal against the subject's skin; and
   allowing the tissue passivation agent to cross-link while the resected anatomical vessel is in the humidified chamber.

2. The method of claim 1, wherein the tissue passivation agent is a photoactive cross-linker and the method further comprises:
   applying light at a suitable wavelength to activate the photoactive cross-linker.

3. The method of claim 1, wherein the tissue passivation agent is a chemical cross-linker.

* * * * *